United States Patent [19]

Ruhenstroth-Bauer et al.

[11] 4,377,514

[45] Mar. 22, 1983

[54] METHOD FOR PRODUCING FACTOR FOR THE STIMULATION OF THE LIVER CELL PROLIFERATION RATE

[75] Inventors: Gerhard Ruhenstroth-Bauer, Gräfelfing; Michel Goldberg; Hubertus Schneider, both of Munich, all of Fed. Rep. of Germany

[73] Assignee: Max-Planck-Gesellschaft zur Foerderung der Wissenschaften E.V., Fed. Rep. of Germany

[21] Appl. No.: 308,355

[22] Filed: Oct. 5, 1981

[30] Foreign Application Priority Data

Oct. 4, 1980 [DE] Fed. Rep. of Germany ....... 3037600

[51] Int. Cl.$^3$ .................... A61K 35/55; A61K 37/02; C07G 7/00
[52] U.S. Cl. ................................. 260/112 R; 424/95; 424/177; 435/268; 435/272
[58] Field of Search ...................... 260/112 R; 429/95; 435/268, 272

[56] References Cited

U.S. PATENT DOCUMENTS 4,330,528  5/1982  Ruhenstroth-Bauer ............ 424/101
4,341,765  7/1982  Ruhenstroth-Bauer ............ 424/101

OTHER PUBLICATIONS

Chem. Abstracts, vol. 92, 1980, Ruhenstroth-Bauer et al., 108428j, Effective date Oct. 18, 1979.

*Primary Examiner*—Howard E. Schain
*Attorney, Agent, or Firm*—Keil & Witherspoon

[57] ABSTRACT

A process for making factor for stimulating the rate of proliferation of liver cells comprising homogenizing animal Peyer's glands, adjusting pH to about 5.5, thermally denaturing the product and recovering the desired factor in the supernatant by centrifugation.

5 Claims, No Drawings

METHOD FOR PRODUCING FACTOR FOR THE STIMULATION OF THE LIVER CELL PROLIFERATION RATE

In German Pat. No. 28 14 981 (corresponding to U.S. Pat. No. 4,341,765) a factor for the stimulation of the liver cell proliferation rate is described; the factor is formed by a protein or proteide which is free of neuraminic acid and has a molecular weight of from 30,000 to 50,000 D. The factor is obtained by homogenizing the remaining livers of test animals which have been partially hepatectomized, bringing them to a pH value of 5.5, and thermally denaturing them at 95° C., and centrifuging them; the resulting product contains the factor. The blood plasma of partially hepatectomized experimental animals can be used as an alternative to the liver remainders of partially hepatectomized experimental animals. This alternative, however, does not yield the factor itself, but rather a preliminary factor, from which the neuraminic acid must be removed through treatment with neuraminidase.

Based on the current scientific nomenclature, the name "hepatopoietin" has been suggested for the factor, which represents a hormone.

The formation of this hormone led to the following hypothesis on a control model: the partially hepatectomized liver (i.e. a liver, a portion of which has been operatively removed) sends a stimulus to an organ for the time being unknown, which in response produces the preliminary factor and releases it in the blood plasma. From the conversion of the preliminary factor by neuraminidase, the actual factor arises, which in the liver itself brings about increased division of the liver cells.

The disadvantage of the method for hepatopoietin extraction described in the above noted patent rests in the fact that the initial material—the residual livers or the blood plasma of the partially hepatectomized animals—requires advance preparation. That is, portions of the liver must first be removed in relatively complicated operations; then a certain waiting period must elapse, so that the induced enrichment of the factor in the liver and plasma, as effected by the suspected control loop, can occur. Then the animals must be killed, the remaining livers removed, and the described process performed.

It is therefore an object of this invention to find further possibilities for production of the factor, particularly a type of production employing the organ actually producing the hepatopoietin. In the past, however, this organ had not been identified.

This objective is achieved by homogenizing the Peyer's glands of the experimental animals, bringing them to a pH value of 5.5, thermally denaturing them at 95° C., and centrifuging them; the resulting product contains the factor.

This solution is based on the knowledge that in mammals hepatopoietin is formed in the so-called Peyer's glands. These are lymph follicles (collections of lymphocytes) at the small intestine, at its opening into the large intestine.

It became apparent that an extract obtained from the Peyer's glands of partially hepatectomized animals has the same effect on the liver cell proliferation rate as the extract obtained according to the procedure described in DE-PS No. 28 14 981. At the same time, however, it became apparent—thus benefitting the procedure considerably for the above-mentioned reasons—that an extract obtained from the Peyer's gland of normal (i.e. not partially hepatectomized) animals basically has the same stimulative effect on proliferation. The extract is produced in the same manner as described in DE-PS No. 28 14 981; i.e. the homogenates of the operatively removed Peyer's glands are brought to a pH level of 5.5, thermally denatured at 95° C., and centrifuged, yielding a product that contains hepatopoietin.

This stimulating effect on proliferation caused by the extract obtained from the Peyer's gland is brought about both without and with—and then to an intensified degree—a following treatment with neuraminidase. It thus seems that both the preliminary factor (which yields the factor after treatment with neuraminidase) and the actual factor itself can be obtained through extraction from the Peyer's glands.

Commercial use is assured by application of the factor among humans. Clinical experiments on humans, however, will not be possible in the foreseeable future. This does not place the commercial usability is question, since, as is shown in the following explanations, it is general specialist knowledge in this field that proteins or proteides obtained in this manne are not species-specific. To document this, reference is made to the following publications:

(a) Iscove, Sieber and Winterhalter, Erythroid Colony Formation in Cultures of Mouse and Human Bone Marrow: Analysis of the Requirements for Erythropoietin by Gel Filtration and Affinity on Agarose-Concanavalin A, J. Cell. Physiol. 83, 309–320.

This publication describes the effectiveness of erythropoietin obtained from the blood plasma of *sheep* on *human* bone marrow cells.

(b) Kroner and Hogan, The Effect of Growth Hormone on Inducible Liver Enzymes, in: Pecile and Müller (eds.). Growth and Growth Hormone (1972), p. 98–105.

This publication describes the effect on rats of a growth hormone obtained from cattle (cf. e.g. the legend on FIG. 3).

(c) Schally and Arimura, Growth Hormone-Releasing Hormone (GH—RH) of the Hypothalamus; its Chemistry and in Vivo and in Vitro Effects, in: Pecile and Müller (eds.), Growth and Growth Hormone (1972), p. 247–251.

This publication describes the effect on rats of a hormone obtained from pigs.

(d) From the following publications: Goldstein, Isolation of Bovine Thymin; a Polypeptide Hormone of the Thymus, Nature, 247, 11 (1974), and Kagan et al., Induction of Human Granulocyte Differentiation in Vitro by Ubiquitin and Thymopoietin, Blood 50, 275–288 (1977) the effect can be seen of thymopoietin obtained from *cattle* on *humans*. The first publication concerns its extraction from cattle, the second its testing on humans.

(e) Furthermore, it is generally known that insulin having an effect on *rats* and *mice* is also effective among *humans*: Garcia, J. F. Assays for Erythropoietin, J. W. Fisher (ed.), Kidney Hormones, 1977, pp. 7–35.

In the following, the formation of an extract will be described. Involved here is extraction from the Peyer's glands of partially hepatectomized experimental animals.

The experiments were performed on female SPF Wistar rats (Institute for Radiation and Environmental Research Institut für Strahlen- and Umweltforschung), Neuherberg/Munich) weighing from 95 to 105 g. The animals were killed and their blood drained, and the Peyer's glands were microsurgically removed. The Peyer's glands, together with a 4-fold (weight) quantity of bi-distilled water, are then homogenized in an Elvehjem-Potter. This pulverizes and as completely as possible destroys the Peyer's gland material. The device mentioned above is state-of-the-art; with it the cells are ground in a glass cylinder, between the cylinder and a teflon spindle rotating within it. The substances contained in the cells are thus prepared for the following concentration and separation processes.

The cell homogenates thus obtained from the Peyer's glands are brought to the pH level with hydrochloric acid (HCl) solution in a concentration of 0.1 N. This acidulation is an important selective step in separating a large number of proteins: they are precipitated out and thus withdrawn from further concentration and isolation. Thus, there remain in the homogenate only those proteins that are stable after acidulation to pH=5.5. That is, they are stable at a numerical value of pH=5.5 (since a numerically small pH value corresponds to a greater degree of acidulation). Following this, the homogenates are thermally denatured at a temperature of 95° C. for a period of 20 minutes. The purpose of this step is to precipitate further component parts, namely, those that are not stable at this or higher temperatures.

With these two steps (acidulation to pH=5.5 and thermal denaturation at 95° C.) a greater portion of the homogenate components are destroyed and thus precipitated. Following this, centrifugation with 4000 g is performed for a period of 15 minutes (Christ minifuge, Osterrode/Harz). The supernatant after centrifugation thus contains only those effective substances contained in the original homogenate that are still stable at pH=5.5 and 95° C., and these in purified form.

In order to obtain those portions of these effective substances that are contained in the precipitates formed from centrifugation, the precipitates were brought to the original volume with bi-distilled water, again acidulated to pH=5.5, thermally denatured at 95° C., and centrifuged. This process was repeated twice.

The supernatants from these three centrifugations were then joined and lyophilized, i.e. subjected to dry freezing with dehydration in a vacuum. This makes them available in powder form and they are stored at −20° C. This substance forms the extract employed in the experiments described below (*TH extract*).

Simultaneously and in the same fashion, an extract was obtained from animals that were not partially hepatectomized. This, then, is the extract from the Peyer's glands of normal animals (*N extract*).

At the same time a portion of the N extract was treated with neuraminidase. To this end, the lyophilized N supernatant was dissolved in bi-distilled water, brought to pH=5.5, and incubated for one hour at 37° C. with 250 N neuraminidase preparation (Behring-Werke, Marburg). The excess neuraminidase was then inactivated at 95° C. for a period of 30 minutes and centrifuged; the resulting product was again lyophilized. The lyophilisate formed the extract, treated with neuraminidase, from the Peyer's glands of normal (i.e. not partially hepatectimized) animals, the *NND extract*.

It was then seen that all extracts brought about an increase in liver cell proliferation. Thus, the TH extract from the Peyer's glands of partially hepatectimized animals *without* subsequent neuraminidase treatment, the N extract from the Peyer's glands of normal animals *without* subsequent neuraminidase treatment, and the NND extract from the Peyer's glands of normal animals *with* subsequent neuraminidase treatment.

To induce proliferation, in each case 1 g of the given extract was dissolved in 0.9% NaCl solution and 2.0 ml of the solution was intraperitoneally (i.p.) injected into normal rats.

The same amount of a 0.9% NaCL solution was likewise intraperitoneally injected into control animals.

Liver cell proliferation after injection of the TH extract was determined by measuring the DNA synthesis. This can be done by measuring the quantity of radioactive substances specifically incorporated in the DNA. The substance employed was $^3H$ methyl thymidine. This has a special activity of 25 Ci/mmol (manufacturer: Radiochem. Center, Amersham).

19 hours after injecting the experimental animals, as well as the control animals, with the extracts TH, N, and NND, 50$\mu$ Ci$^3$H methyl thymidine was in each case injected. The animals were killed after one hour. The liver was removed and stored at −20° C.

Following this, the DNA of the liver was extracted following Weinbren and Woodward (Br. J. Exp. Path. 45, 442–449) 1964. A portion of this extract was used in a radioactivity measurement. For this measurement 1.5 ml of a solution containing PCA (perchloroacetic acid) was neutralized with 0.5 NaOH in a 1N concentration. The resulting solution was (verb missing in original text) in a scintillation glass with 5 ml triton ×100 and 10 ml toluene (0.6 PPO; PPO=1.5 diphenyl oxazol). By means of a scintillation counter (Intertechnique, Paris) the radioactivity was then measured as the number of disintegrations/minute (Dpm). A further portion of the DNA extract was used to measure the DNA concentration following Burton (Biochem. J. 62, 316-323) 1956. In this fashion the specific activity in disintegrations/minute/microgram DNA (DPM/$\mu$g DNA) is determined.

The result was the values given in the following table.

TABLE 1

| Injected with: | TH extract (extract from Peyer's glands of partially hepatectomized test animals) | N extract (extract from Peyer's glands of normal test animals) | NND extract (extract from Peyer's glands of normal test animals; extract treated with neuraminidase) | Control (NaCl solution) |
|---|---|---|---|---|
| DNA synthesis: (Dpm/$\mu$g DNA) | 348 ± 63 n = 4 | 255 ± 74 n = 4 | 329 ± 59 n = 4 | 104 ± 22 n = 12 |

This demonstrates that the i.p. injection of the specified extracts among normal animals results in a considerable intensification of the DNA synthesis, which for its part is a necessary precondition for cell division and thus of liver growth through cell division.

It is of special importance here that an effect could be achieved with the N and NND extracts, i.e. with extracts from the Peyer's gland of normal animals. This means that for the extraction of hepatopoietin, a partial hepatectomy of the animals from which it is extracted is no longer necssary. This considerably simplifies production, and it opens up possibilities for operatively removing the Peyer's glands of slaughter animals and extracting hepatopoietin from them. This also would mean a considerable simplification in production.

The following experiments were performed to further support the fact that the Peyer's glands have the importance described above for the proliferation of liver cells:

Various organs in the abdominal area were removed in segments. A partial hepatectomy was then performed on the same animals and the reaction measured.

Specifically, the following resections were performed on 200 g female SPF Wistar rats, as well as a 70% partial hepatectomy:

(a) Ileotransversotomy (Sham Operation)

Following dissection of the distal ileum, about 4 cm before the opening into the colon, a blind closure was made on the distal ileum stump. This was followed by an ileocolostomy of the oral ileum stump about 2 cm aboral from the ileocecal corner, by means of seromuscular suturing. (In table 2: Ileo).

(b) Partial ileo-colectomy

First the ileocecal corner was prepared. After carefully legating the vessel, a resection of about 4 cm of the distal ileum and about 2 cm of the proximal colon was performed. Following this an end-to-end anastomosis of the ileum stump with the colon stump was performed with a seromuscular intussuscepted suture. In this fashion the part of the ileum containing the Peyer's glands is removed (below: Il-Co).

(c) Resection of Peyer's glands

The entire small intestine was first prepared. After locating the Peyer's glands, a wedge-shaped resection and end-to-end anastomosis, proceeding from the ileocecal corner towards the mouth, were performed with seromuscular suturing. An average of 6 areolae were resected (below: PD).

(d) Colon resection

After preparing the colon a resection of about 3 cm of the colon approx. 2 cm aboral to the ileocecal corner was performed. This was again followed by an end-to-end anastomosis of the two colon stumps (below: Co).

(e) Mesenteric lymph node extirpation

First the mesenteric lymph node chain was prepared, which runs from the ileocecal corner to the radix mesenterii. The individual lymph nodes were then isolated in steps, the vessel hilus ligated, and finally the lymph node resected. Thus the lymph cell areas neighboring the Peyer's glands, and resembling them, were removed, but the Peyer's glands themselves left intact (below: MLK).

(f) X-ray radiation

After preparing the entire intestine, the rats were covered with a thick lead plate. The same intestinal area that was resected in the ileo-colectomy was drawn out through a small crack. The rats were then radiated for 8 minutes with a total of 400 R. The wound was then closed at all layers (below: Rönt.).

The sham operation was likewise performed for control purposes, in order to exclude the possibility that the observed effects were a result of anesthesia, the effect of coldness on the organs, of an operative shock, etc.

To make possible the observation of DNA synthesis among the animals, $50\mu$ $Ci^3H$ thymidine was injected into them 21 h after the operation. Exactly one hour later the rats were killed. The liver was removed and the proliferation rate determined in the manner described above.

The results were the regenerative responses shown in table 2, varying according to the type of resection.

TABLE 2

| Treatment | Ileo | Il-Co | PD | CO | MLK | Ront. |
|---|---|---|---|---|---|---|
| spec. activity in Zpm/µg DNA $\bar{S} \pm SD$ | 889 ±167 | 216 ±116 | 130 ±46 | 912 ±99 | 991 ±139 | 1246 ±220 |
| n | 8 | 5 | 5 | 5 | 4 | 6 |

In relation to the control operation (Ileo), there was a regeneration reduced to 24±11% in the case of the ileo colectomy (II-Co) and when the Peyer's glands were removed, a regeneration of only 18±5%. In the resections in which the Peyer's glands were left intact there was no reduced regeneration. In the case of X-ray radiation there was even a somewhat increased regeneration. This can possibly be explained by the X-ray radiation destroying tissue and thus releasing the factor.

This experiment confirms the significance of the Peyer's glands. That not only a process that is decisive for the formation of the hepatopoietin or for its appearance in the liver as a regenerative response takes place in these glands, but that the hepatopoietin itself is produced there was made apparent only with the experiments described above on the effect of the extract obtained from the Peyer's glands.

Of further significance in the results is the fact that both *without* subsequent treatment with neuraminidase and *with* subsequent treatment with neuraminidase the extract brings about the described increase in the proliferation rate. From this it can be concluded that the extract contains both the preliminary factor (which yields the actual factor when treated with neuraminidase) and the factor itself (which is free of neuraminic acid and therefore is not changed by treatment with neuraminidase).

This may point to the possibility that both substances, both the factor itself and the preliminary factor, are produced by the Peyer's glands. They then reach the liver by way of the v. portae. The liver then seizes the factor, while the preliminary factor is released into the blood, so that it is present in the plasma and yields the factor after reacting with neuraminidase. This would explain the fact that only the preliminary factor, not the factor itself, can be found in the systemic blood plasma.

The foregoing description of our invention has been directed to particular details in accordance with the requirements of the Patent Act and for purposes of explanation and illustration. It will be apparent, however, to those skilled in this art that many modifications and changes may be made without departing from the scope and spirit of the invention. It is further apparent that persons of ordinary skill in this art will, on the basis of this disclosure, be able to practice the invention within a broad range of process conditions. It is our intention in the following claims to cover all such equivalent modifications and variations as fall within the true scope and spirit of our invention.

We claim:

1. A process for producing a factor for stimulating the rate of proliferation of liver cells which comprises homogenizing the Peyer's glands of animals, adjusting the pH of the homogenized product to approximately 5.5, thermally denaturing the pH adjusted product, and centrifuging the denatured product to provide a supernatant containing said factor.

2. A process as defined in claim 1 wherein said thermal denaturing is carried out at a temperature of approximately 95° Centrigrade.

3. A process as defined in claim 2 wherein said pH is adjusted by acidifying the homogenized product.

4. A process as defined in claim 3 which further comprises treating the supernatant with neuraminidase to remove neuraminic acid.

5. A process as defined in any of claims 1, 2, 3 or 4, wherein said glands are the Peyer's glands of partially hepatectomized animals.

* * * * *